United States Patent [19]

Klinvex

[11] Patent Number: 4,643,029
[45] Date of Patent: Feb. 17, 1987

[54] ULTRASONIC PROBE FOR THE REMOTE INSPECTION OF NUCLEAR REACTOR VESSEL NOZZLES

[75] Inventor: Daniel E. Klinvex, McKeesport, Pa.

[73] Assignee: Westinghouse Electric Corp., Pittsburgh, Pa.

[21] Appl. No.: 546,603

[22] Filed: Oct. 27, 1983

[51] Int. Cl.$^4$ .................. G01N 24/04; G21C 17/00
[52] U.S. Cl. ............................. 73/632; 376/249; 376/252
[58] Field of Search ................ 376/249, 252; 73/632, 73/661

[56] References Cited

U.S. PATENT DOCUMENTS 4,131,018 12/1978 Muller et al. ............ 376/249
4,232,271 2/1984 Wentzell et al. ......... 376/249
4,474,064 10/1984 Naruse et al. ........... 376/249
4,526,037 7/1985 Wenzell et al. .......... 376/249
4,532,808 8/1985 Wentzell et al. ......... 376/249

Primary Examiner—Salvatore Cangialosi
Attorney, Agent, or Firm—L. A. DePaul

[57] ABSTRACT

An ultrasonic probe for the weld inspection of nuclear reactor vessel nozzles is constructed from a plurality of segments interconnected by means of a flexible joint and protected by bumpers of various shapes. The probe is capable of successfully operating in an underwater and radioactive environment under remote control while maintaining a high degree of control over the placement and movement of the included transducer assembly for performing contact type testing. The transducer assembly, which includes an ultrasonic transmitter and receiver, is mounted within an ultrasonic sensor body which permits insertion of the probe within a nozzle of a reactor vessel while maintaining direct surface to surface contact with the nozzle for weld area examination by contact type testing.

26 Claims, 2 Drawing Figures

ULTRASONIC PROBE FOR THE REMOTE INSPECTION OF NUCLEAR REACTOR VESSEL NOZZLES

BACKGROUND OF THE INVENTION

The present invention relates in general to an ultrasonic test probe for inspecting an object from a remote location for locating defects therein, and more particularly, to such a probe for the inspection by means of contact type ultrasonic examination of an object, such as for example the weld areas of various nozzles provided on a nuclear reactor vessel for locating defects therein, such as cracks, voids and the like, while present in an underwater radioactive environment.

Commercial nuclear reactor vessels used in the generation of electrical power are of the pressurized water or boiling water type. In either case, the reactor vessel is generally constructed of a cylindrical metallic shell having a plurality of circumferentially spaced nozzles extending through the shell wall and welded thereto. These nozzles are of various types and are often referred to as safety injection nozzles, outlet nozzles and inlet nozzles. Thus, it can be appreciated that numerous welds are required in the fabrication of the reactor vessel, such as in securing the various nozzles to the shell wall. Although the weld areas of the reactor vessel are, of course, inspected prior to the reactor vessel's initial use, government regulations mandate in-service inspection of the reactor vessel welds.

Under such regulations, it is required that the vessel weld areas be subjected to periodic volumetric examination, whereby the structural integrity of the weld is monitored. Due to the nature of such an in-service inspection, the device designed to accomplish the specific weld examinations of the numerous nozzles must be capable of successfully operating in an underwater and radioactive environment and under remote control while maintaining a high degree of control over the placement and movement of the inspection sensors. It has been known to use ultrasonic transducers as the inspection sensors for inspecting the numerous welds of the reactor vessel using the socalled space type testing. However, in some instances, it is preferred, if not required, that the ultrasonic transducers be employed in contact type testing where the transducers are manipulated into direct contact with the surface of the nozzle at a location adjacent the weld to be examined. It is therefore desired in some instances that the ultrasonic transducers be arranged on a probe which can be inserted and manipulated within the interior of these nozzles while, for example, being in an underwater environment, and having sufficient flexibility to allow direct contact between the transducers and the examination surface of the nozzles, thereby allowing for such contact type testing.

Although there has been known the use of ultrasonic transducers mounted to a probe for inspecting the nozzle welds of a reactor vessel by space type testing, there has heretofore been unknown a flexible probe adapted for use with such transducers which permits a high degree of control over the placement and movement of the transducers to permit contact type testing in an underwater radioactive environment. Accordingly, it can be appreciated that there remains an unsolved need for such a probe for use in conducting weld examinations of reactor vessel nozzles using contact type testing.

SUMMARY OF THE INVENTION

It is broadly an object of the present invention to provide an ultrasonic probe for the inspection of an object by means of contact type testing techniques, and in particular, for one which overcomes or avoids one or more of the foregoing disadvantages resulting from the use of the above-mentioned prior art probes, and which fulfills the specific requirements of such a probe. Specifically, it is within the contemplation of one aspect of the present invention to provide an ultrasonic probe for the weld inspection of nuclear reactor vessel nozzles, such as injection, inlet and outlet nozzles, remotely in an underwater radioactive environment, and from inside the reactor vessel using contact type testing.

A further object of the present invention is to provide an ultrasonic probe for the inspection of an object, such as the weld area of a nuclear reactor vessel nozzle, which maintains a high degree of control over the placement and movement of the ultrasonic transducers with respect to the object being examined.

A still further object of the present invention is to provide an ultrasonic probe for the inspection of an object, which prevents damage to the objects during insertion and manipulation of the probe while performing contact type testing.

A yet still further object of the present invention is to provide an ultrasonic probe for the weld inspection of nuclear reactor vessel nozzles in accordance with government regulations.

A yet still even further object of the present invention is to provide an ultrasonic probe for the inspection of objects by straight and angle beam scanning techniques, such as ultrasonic beams having nominal angles of 45° and 60° with respect to a pependicular to the examination surface.

In accordance with the present invention there is disclosed a probe for inspecting an object for locating defects therein. The probe is constructed of a body having an axis and insertable within the object, sensing means movably arranged within the body along the axis for sensing defects within the object, and biasing means for biasing the sensing means outwardly along the axis of the body while permitting inward movement thereof, the biasing means being operative to cause contact of the sensing means with a portion of the object to be examined when the body is inserted within the object, the sensing means contacting a portion of the object when biased outwardly while permitting relative movement between the sensing means and the object for permitting positioning of the sensing means at successive locations within the object by relative movement between the body and the object.

Further in accordance with the present invention, there is disclosed a probe for inspecting a tubular object from a remote location for locating defects therein, the probe is constructed of an elongated body insertable with the object, the body including a plurality of segments connected end-to-end to define a longitudinally extending axis, a plurality of flexible couplings connecting adjacent pairs of segments together, a transducer assembly movably arranged within the body along a transverse axis extending transversely of the longitudinal axis for locating defects within the object, holding means for holding the transducer assembly within the body, and urging means for urging the holding means outwardly of the body along the radial axis while permitting inward movement thereof along the axis, the transducer assembly contacting an internal portion of the object when urged outwardly by the urging means while permitting relative movement between the transducer assembly and the object for permitting repositioning of the transducer assembly at successive locations internally of the object.

BRIEF DESCRIPTION OF THE DRAWINGS

The above description, as well as further objects, features and advantages of the present invention will be more fully understood by reference to the following detailed description of a presently preferred, but nonetheless illustrative, ultrasonic probe for the inspection of an object, such as a nuclear reactor vessel nozzle, when taken in conjunction with the accompanying drawings, wherein.

DETAILED DESCRIPTION

Figure 1:
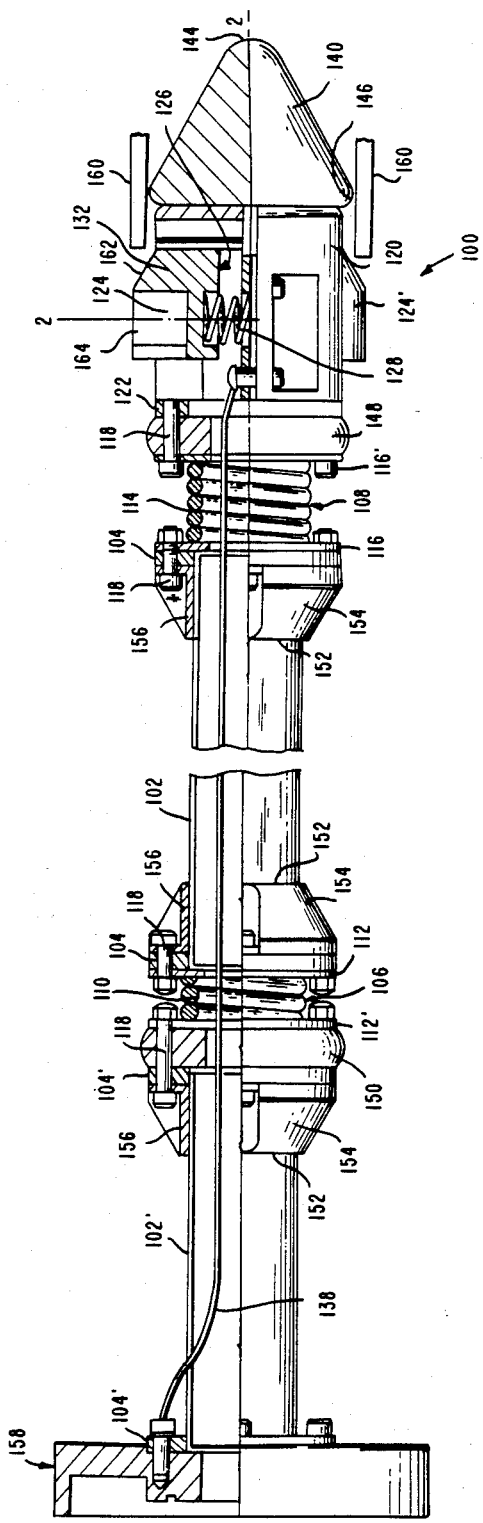
FIG. 1 is a front elevational view, in partial cross-section, showing the ultrasonic probe of the present invention constructed of a pair of hollow tubular segments connected end-to-end by a pair of flexible couplings and having thereat, protective circumscribing bumpers, a pair of radially spaced transducer assemblies and a cone shaped protective bumper secured to the free end of the probe.

Referring generally to the drawings, wherein like reference characters represent like elements, there is shown in FIG. 1 an ultrasonic probe in accordance with the present invention generally designated by reference character 100, which is particularly useful in connection with the weld inspection of nuclear reactor vessel nozzles. However, it is to be appreciated that the probe 100 in accordance with this present invention can also be used in connection with inspection of other types of objects by means of ultrasonic contact type testing techniques.

The probe 100 is constructed of a pair of longitudinally extending tubular segments 102, 102', each segment having at its respective terminal ends a flange 104, 104' arranged normal to the longitudinal axis of the segments and welded thereto. The segments 102, 102' are connected together in end-to-end relationship by a pair of flexible couplings 106, 108. Coupling 106 is constructed of a coiled spring 110 welded between a pair of parallel spaced flanges 112, 112'. Likewise, the coupling 108 is constructed of a coiled spring 114 welded between a pair of parallel spaced flanges 116, 116'. As shown, the spring 114 is provided having more turns than the spring 110 to provide the coupling 108 with greater flexibility than the coupling 106.

As shown, the segments 102, 102', are connected together by the flexible coupling 106 using a plurality of circumferentially arranged bolts 118. That is, flange 112' of the coupling 106 is connected to the flange 104' of the segment 102' while the other flange 112 of the coupling is connected to the flange 104 of the segment 102. In this manner, a pair of adjacent segments, for example, segments 102, 102' may be flexibly coupled in end-to-end relationship to form a longitudinally extending flexible probe 100. Although there has thus far been described the connection of only a pair of segments 102, 102', it is to be understood that any number of such segments may be connected in a similar end-to-end manner so as to provide a probe 100 of any desired length. Further, the couplings 106, 108 may be provided with springs 110, 114 having different flexibilities by increasing or decreasing the number of coils of each spring so as to provide the desired flexibility of the probe 100 at desired locations along its length.

An ultrasonic sensor body 120 is connected to the segment 102 in end-to-end relationship using the coupling 108 in a similar manner as described with respect to the flexible connecting of the segments 102, 102' by means of the coupling 106. That is, the ultrasonic sensor body 120 is provided with a flange 122 which is secured to the flange 116' of the coupling 108 by means of a plurality of circumferentially arranged bolts 118. Similarly, the flange 116 of the coupling 108 is connected to the flange 104 of the segment 102 by means of a plurality of circumferentially arranged bolts 118.

Figure 2:
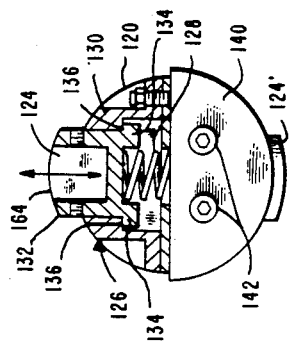
FIG. 2 is a partial cross-section of the probe of the present invention taken along line 2—2 of FIG. 1 showing one transducer assembly outwardly biased along the radial axis of the probe while permitting inward movement thereof.

As more clearly shown in FIG. 2, the ultrasonic sensor body 120 is constructed of a transducer assembly 124 including an ultrasonic transmitter and receiver, and a biasing assembly 126. The ultrasonic transmitter and receiver of the transducer assembly 124 can be of conventional construction, and in accordance with the present invention, may be arranged within the transducer assembly to emit an ultrasonic beam normal to and at predetermined angles, such as 45° and 60°, with respect to a perpendicular to the examination surface, i.e., the interior surface of a nozzle whereat welds are to be inspected. The biasing assembly 126 is constructed of a spring 128, a guide 130 and a holder 132 within which the transducer assembly 124 is mounted. The holder 132 is slidably mounted within the guide 130 along the radial axis of the ultrasonic sensor body 120 for movement in a radial outward and inward direction as indicated by the arrow. The permitted radial outward movement of the holder 132 is limited by the engagement of the tabs 134 projecting outwardly from the holder with the inwardly projecting lips 136 of the guide 130.

The holder 132 and transducer assembly 124 are biased outwardly along the radial axis of the ultrasonic sensor body 120 by means of the spring 128, the compression of such spring permitting radially inward movement of the holder and transducer assembly. Although the present invention has been described as including a single transducer assembly 124 having an ultrasonic transmitter and receiver therein, it is to be understood that a second transducer assembly 124' may also be provided, as well as any additional transducer assemblies as desired. As shown, the transducer assembly 124' is arranged along the radial axis of the ultrasonic sensor body 120 and circumferentially spaced about 180° from transducer assembly 124, although other circumferentially spaced arrangements may be provided. Thus, where additional transducer assemblies 124, 124' are provided, likewise additional biasing assemblies (not shown) will also be provided. As shown in FIG. 1, the electrical operation of the transducer assemblies 124, 124' is accomplished from a remote location by means of control lines 138 which transmit command signals to the ultrasonic transmitter and receive response signals from the ultrasonic receiver.

As previously noted, in order to perform the required ultrasonic testing for locating weld defects within the nozzles of the reactor vessel, it is required that the probe 100 be manipulated into the nozzle through its opening and positioned at various locations along its length adjacent the weld areas to be inspected. As these nozzles are susceptible to damage, it is required that the probe 100 be manipulated to avoid abrupt engagement with the mouth of the nozzles or internally along the surface thereof. For this purpose, a plurality of nylon bumpers of various shapes are secured to the probe 100. Specifically, the free end of the probe 100 is provided with a cone shaped bumper 140 secured thereto by a plurality of bolts 142. The cone shaped bumper 140 has a gently rounded tip 144 and a diameter at its base 146 dimensioned slightly smaller than the inside diameter of the nozzles to be inspected. A donut shaped bumper 148 is sandwiched between the flange 116' of the coupling 108 and the flange 122 of the ultrasonic sensor body 120. In a similar arrangement, a donut shaped bumper 150 is sandwiched between the flange 104' of the segment 102' and the flange 112' of the coupling 106. The donut shaped bumpers 148, 150 are held in their respective position by the circumferentially arranged bolts 118.

As shown, the edges of the donut shaped bumpers 148, 150 have a slight curvature and a diameter generally corresponding to the diameter of the base 146 of the cone shaped bumper 140. The donut shaped bumpers 148, 150 are constructed of radial segments, for example, two or three such segments and secured in a donut shape by means of the bolts 118. However, the donut shaped bumpers 148, 150 may be formed as an integral ring. In addition to the cone shaped bumper 140 and donut shaped bumpers 148, 150, there is provided a plurality of truncated bumpers 152 each having a cam surface 154. The truncated bumpers 152 are secured to the flanges 104, 104' of the segments 102, 102' by means of L-shaped buffer brackets 156. The truncated bumpers 152 and the buffer brackets 156 may be formed in circumferential segments, for example, two or three circumferential segments, or may be provided by unitary construction. The truncated bumpers 152, in addition to guiding the probe 100 within the mouth of a nozzle by means of the cam surface 154, prevent engagement of such nozzle with the flanges 104, 104'.

Briefly in use, the end of the probe 100, that is flange 104' of the segment 102', is connected to a segmented manipulator arm 158 adapted for manipulation of the probe 100 in an underwater and radioactive environment under remote control while maintaining a high degree of control over the placement and movement of the transducer assemblies 124, 124'. Specifically, the probe 100 is connected to the B-axis of the manipulator arm 158 for manipulating the probe into and within the nozzles of the reactor vessel. A suitable segmented manipulator arm 158 for use with the probe 100 of the present invention is disclosed in U.S. Pat. No. 4,196,049, which patent is assigned to the same assignee of the present invention. The manipulator arm 158 is used to position the tip 144 of the cone shaped bumper 140 centrally within the mouth of a nozzle 160 of the reactor vessel to be inspected. In this manner, the cone shaped bumper 140 guides the probe 100 into the nozzle 160 while preventing damage thereto.

As the probe 100 is further inserted into the nozzle 160, the nozzle engages a cam surface 162 provided on the holder 132 of the biasing assembly 126. As the end of the nozzle slides along the cam surface 162, the transducer assembly 124 within the holder 132 is urged downwardly against the opposing force of the spring 128 until the interior surface of the nozzle is in direct contact with the curved surface 164 of the transducer assembly. The radius of curvature of the curved surface 164 of the transducer assembly 124 can be designed to correspond to the radius of curvature of the nozzle 160 to affect a greater contact surface area. As can now be appreciated, the spring 128 maintains direct and positive contact between the transducer assembly 124 and the interior surface of the nozzle 160. However, the spring 128 further permits the inward movement of the transducer assembly 124 such that the probe 100 may be further inserted within the nozzle 160 to its desired locations.

As the probe 100 is continuously inserted into the nozzle 160, the donut shaped bumpers 148, 150 maintain the probe centrally aligned within the nozzle. The flexible couplings 106, 108 minimize the stress that would be applied to the nozzle 160 as a result of any misalignment between the manipulator arm 158 and the nozzle while the probe 100 is inserted therein. In this regard, the coupling 108 being more flexible than the coupling 106, greatly reduces any such stress resulting from misalignment during the initial inserting of the probe 100 within the nozzle. As the probe 100 is further inserted within the nozzle, the cone shaped bumper 140 and donut shaped bumpers 148, 150 self-align the probe 160 therein such that the coupling 106 may be less flexible than the coupling 108. It can therefore be appreciated that the degree of flexibility of the couplings 106, 108 may be varied from joint-to-joint as required.

The truncated bumpers 152, in addition to preventing contact between the nozzle 160 and the flanges 104, 104', are arranged such that their cam surfaces 154 will engage the mouth of the nozzle during the insertion of the probe 100 therein. In this manner, the engagement of the nozzle 160 with the cam surfaces 154 of the truncated bumpers 152, will cause a further centering of the probe 100 in the same manner as described with respect to the cam surface 162 of the holder 132. Thus, the probe 100 of the present invention is adapted for successful underwater operation in a radioactive environment under remote control by the manipulator arm 158 while maintaining a high degree of control over the placement and movement of the transducer assemblies 124, 124' in order to affect contact type testing.

Although the invention herein has been described with reference to particular embodiments, it is to be understood that these embodiments are merely illustrative of the principals and application of the present invention. It is therefore to be understood that numerous modifications may be made in the illustrious embodiments and that other arrangements may be devised without departing from the spirit and scope of the present invention defined by the appended claims.

What is claimed is:

1. A probe for inspecting an object for locating defects therein, said probe comprising an elongated body which is insertable within an opening in said object, a sensing means movably arranged within said body for sensing defects within said object, and biasing means for biasing said sensing means away from the longitudinal axis of said body while permitting movement toward said axis, said biasing means being operative to cause contact of said sensing means with a portion of said object to be examined when said body is inserted within an opening in said object, wherein said elongated body is formed from a plurality of segments interconnected in end-to-end relationship by resiliently flexible couplings having different elasticities in order to reduce stress on the object resulting from misalignment between the probe and the opening in said object.

2. The probe of claim 1 wherein said sensing means comprises a transducer assembly having an ultrasonic transmitter and receiver.

3. The probe of claim 1 wherein said sensing means comprises a pair of transducer assemblies each having an ultrasonic transmitter and receiver.

4. The probe of claim 3 wherein said sensing means is biased along a radial axis of said elongated probe.

5. The probe of claim 4 wherein said transducer assemblies are arranged along said radial axis of said body and circumferentially spaced about 180° from each other.

6. The probe of claim 1 further including a first flexible coupling connecting a front segment and a middle segment together.

7. The probe of claim 6 further including a second flexible coupling connecting a a middle segment and a rear segment together.

8. The probe of claim 7 wherein said first flexible coupling is substantially more flexible than said second flexible coupling.

9. The probe of claim 7 wherein said first and second flexible couplings comprise a spring member.

10. The probe of claim 6 wherein said segments comprise cylindrical tubes.

11. The probe of claim 6 further including guide means for guiding said body within said object.

12. The probe of claim 11 wherein said guide means includes a plurality of bumpers, each of which is circumferentially arranged around said segments adjacent the ends thereof.

13. The probe of claim 12 wherein each of said bumpers is of segmented construction.

14. The probe of claim 12 wherein each of said bumpers includes a cam surface for engagement with said object.

15. The probe of claim 1 wherein said elongated body includes a front end having guide means attached thereto for guiding said free end within said object.

16. The probe of claim 15 wherein said guide means includes a bumper of conical shape.

17. The probe of claim 1 wherein said biasing means comprises a holder for said sensing means and urging means for urging said holder outwardly of said body along a radial axis thereof.

18. The probe of claim 17 wherein said urging means comprises a spring.

19. The probe of claim 17 wherein said holder includes a cam surface for engaging said object whereby said holder is moved inwardly along said radial axis of said body as said body moves said holder along the surface of the object.

20. A probe of inspecting a tubular object from a remote location for locating defects therein, said probe comprising an elongated body insertable within said object, said body including a plurality of segments connected end-to-end to define a longitudinally extending axis, a plurality of resiliently flexible couplings connecting adjacent pairs of segments together, a transducer assembly movably arranged within said body along a transverse axis extending transversely of the longitudinal axis for locating defects within said object, holding means for holding said transducer assembly within said body, and urging means for urging said holding means outwardly of said body along said radial axis while permitting inward movement thereof along said axis, and a bumper means circumscribing each of said flexible couplings for both absorbing mechanical shock between the probe and the tubular object, and for guiding the probe into and within the interior of the object.

21. The probe of claim 20 wherein said flexible couplings have substantially different flexibilities in order to reduce stress on the object resulting from misalignment between the probe and the interior of the tubular object.

22. The probe of claim 21 wherein each of said bumper means includes a cam surface for engaging portions of said object.

23. The probe of claim 21 wherein said body has a front end having a bumper in the shape of a cone attached thereto for centering said body within said object during the insertion thereof.

24. The probe of claim 20 wherein said transverse axis comprises a radial axis of said body.

25. The probe of claim 24 wherein said holding means includes a cam surface for engaging said object whereby said holding means is moved inwardly along said radial axis against said urging means.

26. A probe for inspecting an object for locating defects therein, said probe comprising an elongated body which is insertable within an opening in said object, a sensing means movably arranged within said body for sensing defects within said object, and biasing means for biasing said sensing means away from the longitudinal axis of said body while permitting movement toward said axis, said biasing means being operative to cause contact of said sensing means with a portion of said object to be examined when said body is inserted within an opening in said object, wherein said elongated body is formed from a plurality of segments interconnected in end-to-end relationship by resiliently flexible couplings, each of which is circumscribed by a bumper means for both absorbing mechanical shock and for guiding said probe into said opening and aligning said probe within said object.

* * * * *